United States Patent [19]

Chen et al.

[11] Patent Number: 5,702,432
[45] Date of Patent: Dec. 30, 1997

[54] INTRACORPOREAL LIGHT TREATMENT OF BLOOD

[75] Inventors: James C. Chen, Bellevue, Wash.; Brent Wiscombe, Mesa, Ariz.

[73] Assignee: Light Sciences Limited Partnership, Redmond, Wash.

[21] Appl. No.: 725,578

[22] Filed: Oct. 3, 1996

[51] Int. Cl.$^6$ .................................................. A61N 00/00
[52] U.S. Cl. .................................. 607/88; 604/6; 604/21
[58] Field of Search ............................ 607/89, 88, 92; 604/20, 21, 4–5, 6; 435/238

[56] References Cited

U.S. PATENT DOCUMENTS

| | | | |
|---|---|---|---|
| 4,878,891 | 11/1989 | Judy et al. | 604/5 |
| 4,915,683 | 4/1990 | Sieber | 604/4 |
| 5,030,200 | 7/1991 | Judy et al. | 604/5 |
| 5,261,874 | 11/1993 | Castle | 604/4 |

(List continued on next page.)

OTHER PUBLICATIONS

Bisaccia, Emil, et al., "Extracorporeal Photopheresis in the Treatment of AIDS–Related Complex: A Pilot Study," ©1990 American College of Physicians, *Annals of Internal Medicine*, 1990; 113:270–275.

Itoh, T., et al., "Merocyanine 540–sensitized photoinactivation of high–grade non–Hodgkin's lymphoma cells: potential application in autologous BMT," © Macmillan Press Ltd., 1993, *Bone Marrow Transplantation*, 1993, 12:191–196.

Jamieson, C.H.M., et al., "Preferential Uptake of Benzoporphyrin Derivative By Leukemic Versus Normal Cells," *Leukemia Research*, vol. 14, No. 3, pp. 209–219, 1990, Printed in Great Britain.

Knobler, R.M., et al., "Extracorporeal Photochemotherapy for the Treatment of Systemic Lupus Erythematosus," *Arthritis and Rheumatism*, vol. 35, No. 3, Mar. 1992, pp. 319–324.

R.G. Landes Company, Austin, Texas, "Medical Intelligence Unit, Extracorporeal Photochemotherapy: Clinical Aspects and the Molecular Basis for Efficacy," Chapter 1, ©1994 R.G. Landes Company, Library of Congress Cataloging–in–Publication Data, ISBN 1–57059–071–0, Catalog No. LN9071, 13 pp.

Lim, H.W., et al., "Photopheresis for the Treatment of Cutaneous T–Cell Lymphoma," Hematology/Oncology Clinics of North America, vol. 9, No. 5, Oct. 1995, pp. 1117–1126.

Malawista, S.E., et al., "Treatment of Rheumatoid Arthritis by Extracorporeal Photochemotherapy, A Pilot Study," Arthritis and Rheumatism, vol. 34, No. 6, Jun. 1991, pp. 646–654.

*Primary Examiner*—Jennifer Bahr
*Assistant Examiner*—Ryan Carter
*Attorney, Agent, or Firm*—Ronald M. Anderson

[57] ABSTRACT

A method and apparatus for administering intracorporeal photopheresis to blood flowing in a patient's body to destroy an undesirable component in the blood, where the undesirable component has absorbed a photoreactive agent having a characteristic light absorption waveband. The apparatus includes an implantable housing that is adapted to be placed transcutaneously within a patient's body. An inlet and outlet for a fluid path through the housing are provided and are coupled to a patient's circulatory system so that they convey blood into and out of the housing. Light sources disposed within the housing(or externally disposed and coupled to the housing by optical fibers) emit light having a waveband substantially equal to the absorption waveband of the photoreactive agent. A portion of the fluid path within the housing is optically transparent so that blood is irradiated with light from the light source. The fluid path can have one of several different configurations, including serpentine, planar coil, helical coil, and cross tubes coupling inlet and outlet header manifolds. The light source can comprise light emitting diodes (LEDs) or other types of light sources and may be coupled to the reactor through optical fibers. The power supply for the light source can be intracorporeal or extracorporeal.

26 Claims, 4 Drawing Sheets

U.S. PATENT DOCUMENTS

| | | | |
|---|---|---|---|
| 5,263,925 | 11/1993 | Gilmore, Jr. et al. | 604/21 X |
| 5,290,221 | 3/1994 | Wolf, Jr. et al. | 604/4 |
| 5,300,019 | 4/1994 | Bischof et al. | 604/4 |
| 5,429,594 | 7/1995 | Castle | 604/4 |
| 5,445,608 | 8/1995 | Chen et al. | 607/89 X |
| 5,501,662 | 3/1996 | Hofmann | 604/20 |
| 5,527,704 | 6/1996 | Wolf, Jr. et al. | 435/283.1 |

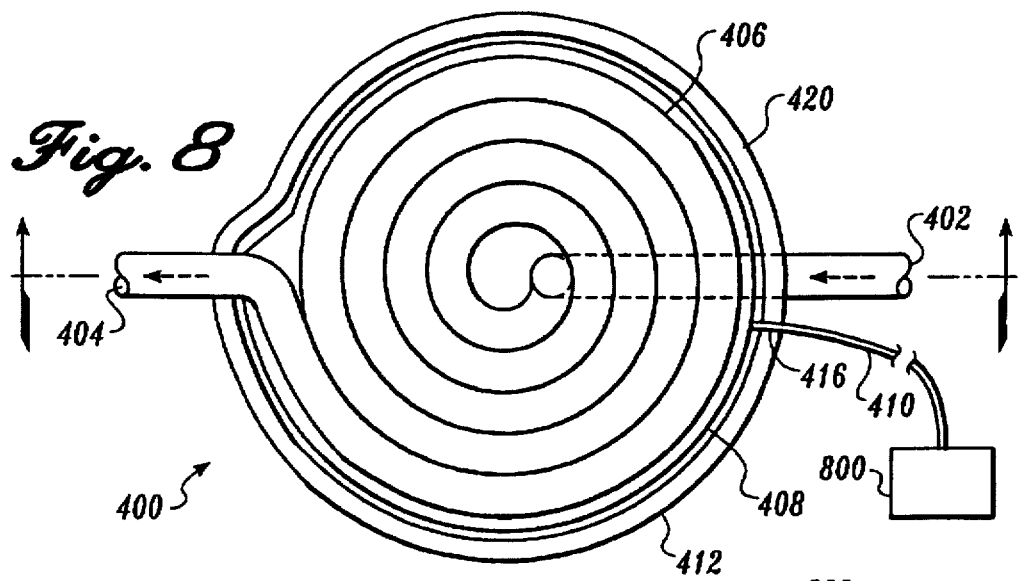
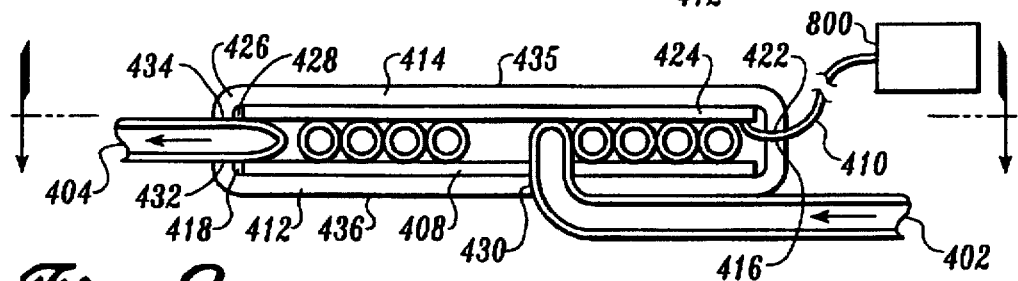
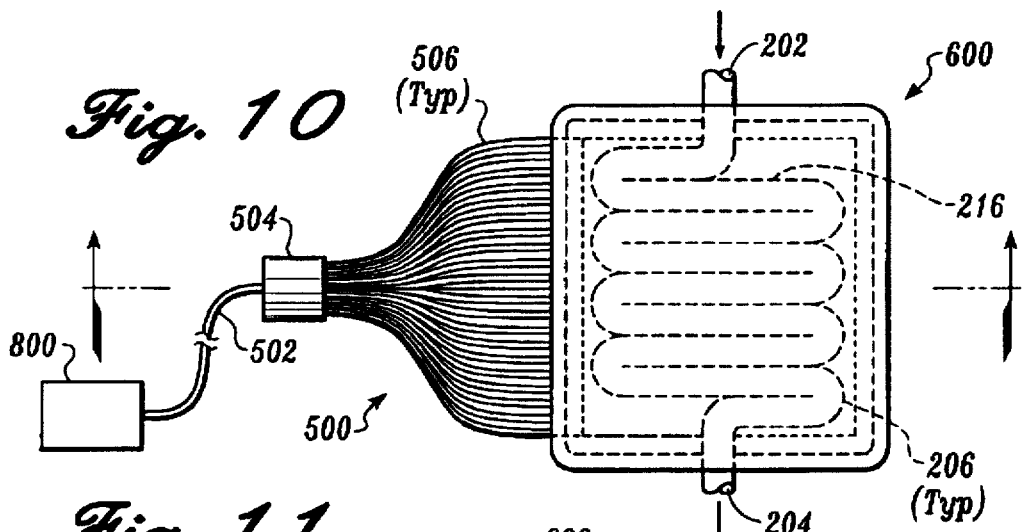
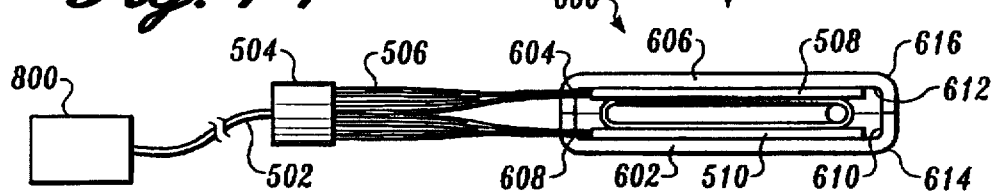

INTRACORPOREAL LIGHT TREATMENT OF BLOOD

FIELD OF THE INVENTION

The present invention generally relates to an invention for using light to administer a medical treatment to blood, and more specifically, to apparatus and a method for exposing blood circulating through a patient's body to light, for the purpose of providing a therapeutic benefit.

BACKGROUND OF THE INVENTION

Various diseases of the blood, such as T-cell lymphoma, can be best treated by a technique that affects only a selected type of organism in the blood to avoid undesired consequences relating to the other functions that blood performs. Extracorporeal photochemotherapy or photopheresis is currently a preferred treatment for such diseases. In this therapy, heparinized venous blood is treated with a photosensitizing agent such as 8-methoxypsoralen (which may be ingested orally). The photosensitizing agent, which is preferentially absorbed by abnormal or malignant T-cell lymphocytes that are to be destroyed, is circulated outside the body and exposed to UVA light having a waveband corresponding to an absorption waveband of the psoralen. After being exposed to the light source, the blood is returned to the patient's body. The extracorporeal photodynamic therapy (PDT) of blood in this manner is typically done at a hospital or other medical facility and is a relatively time consuming procedure (e.g., up to six hours or possibly more per treatment, repeated on consecutive days, at monthly intervals) that has a substantial impact on the life of the patient undergoing the therapy. Furthermore, because photochemotherapy of blood is only available at certain medical institutions, it may be necessary for a patient to travel some distance in order to reach a place where the treatment can be obtained.

It is impractical to provide extracorporeal photochemotherapy of blood for very extended periods of time. Accordingly, the full potential of the photopheresis treatment may not be realized. In addition, the patient is placed at risk of incurring an infection each time that the treatment is performed, since catheters conveying the blood to and from the body are invasively connected to the circulatory system of the patient.

Clearly, it would be much more desirable to provide for intracorporeal photopheresis of blood, using an apparatus disposed in situ within the patient's body. Such a device could be used to expose a patient's blood to light after an appropriate photoreactive agent had been administered orally, percutaneously, or intravascularly. By employing an implanted device to expose the blood to light during photopheresis, a patient could remain fully ambulatory during the treatment and the effect of the treatment on the patient's life would be minimal. More importantly, by using an implanted device to provide internal photopheresis of the blood, the treatment can repetitively be provided at any selected interval of time, or if desired, on a continuous basis, and with minimal risk of infection or other adverse side effects.

By administering the treatment to a patient's blood for extended periods of time in situ, using various levels of light, it is believed that improved results will be obtained compared to the relatively short duration conventional extracorporeal light therapy that is currently employed. Furthermore, light sources employed in an implanted device are much less likely to cause damage to other components of a patient's blood than the banks of UVA lights used in the current extracorporeal apparatus, yet should be very effective in destroying or adversely affecting malignant T-cell lymphocytes or other undesired organisms or constituents in the blood.

The effectiveness of light emitted by an implanted probe for use in administering photodynamic therapy (PDT) to abnormal tissue at internal treatment sites is disclosed in commonly assigned U.S. Pat. No. 5,445,608, the drawings and disclosure of which are specifically incorporated herein by reference. Each of the different embodiments for the probes disclosed in this reference includes a plurality of light sources that are mounted so that the light emitted thereby is transmitted to the cells to be destroyed by PDT. The light sources used on the probes taught by this reference are preferably light emitting diodes (LEDs). By transcutaneously placing one of these probes at an internal treatment site and applying PDT for an extended time, abnormal tissue at the treatment site can be destroyed without adverse impact on surrounding normal tissue. However, none of the embodiments disclosed in this patent is suitable for photopheresis treatment of blood. Accordingly, a different type of device must be provided for this purpose.

SUMMARY OF THE INVENTION

In accordance with the present invention, apparatus are defined for administering intracorporeal photopheresis to blood flowing in a patient's body to destroy an undesirable component in the blood, where the undesirable component has absorbed a photoreactive agent having a characteristic light absorption waveband. The apparatus includes an implantable housing adapted to be transcutaneously placed at a site within a patient's body, being made of a biocompatible material. An inlet port and an outlet port are provided in the housing and are adapted to couple to a patient's circulatory system to convey the blood circulated thereby into and out of the housing. A light source disposed within the housing emits light having a waveband substantially equal to the absorption waveband of the photoreactive agent. Electrical current to energize the light source is provided by a power source. A fluid path is disposed within the housing, adjacent to the light source and in fluid communication with the inlet port and outlet port. At least a portion of the fluid path is optically transparent, so that blood circulating through the fluid path is irradiated with the light emitted by the light source to effect the light treatment.

The fluid path preferably comprises one of several different shaped passages, depending upon the embodiment. Various embodiments thus comprise either a serpentine shaped passage, a helically-coiled passage, a substantially planar coil, or a plurality of parallel passages extending between two headers. In the latter embodiment, one of the two headers is coupled to the inlet port and the other header is coupled to the outlet port.

Also, different embodiments employ various types of light sources. One such light source comprises a generally planar array of spaced-apart light emitting devices, which is preferably coupled with another generally planar array of spaced-apart light emitting devices. The arrays are disposed at opposite sides of the fluid path, and the light emitting devices are directed so as to emit light toward the fluid path. In addition, the light emitting devices are preferably mounted on a substantially light reflecting surface. In another embodiment, the light source comprises a bar that includes a plurality of light emitting devices, which are spaced apart generally along a longitudinal axis of the bar.

In yet another embodiment, the light source comprises a plurality of optical fibers that are coupled to a light emitting device.

In one embodiment, the power source is integral with the housing. Alternatively, however, the power source may be disposed within an enclosure comprising a biocompatible material and is thus adapted to be implanted within the patient's body, separate from the housing for the light source.

The housing may include a tab that is usable for securing the housing at a desired location within the patient's body. For example, sutures can be threaded through a hole in the tab to secure the housing to an adjacent rib or other structure within the patient's body. It is also desirable that the housing have a substantially light reflective inner surface to improve the irradiation of blood flowing therethrough.

To facilitate coupling the fluid path into the patient's circulatory system, the inlet port and the outlet port preferably comprise vascular graft tubing. The vascular graft tubing enables a physician to suture the vascular graft tubing to the ends of a transected blood vessel within the patient's body. To avoid clotting, an inner surface of the fluid path may be coated with a substance, such as heparin, which resists the formation of blood clots.

Another aspect of the present invention is directed to a method for treating blood flowing in a patient's body to destroy an undesirable component. The method includes steps that are generally consistent with the functions described above in connection with the apparatus used for administering intracorporeal photopheresis of blood.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 8 is a cross-sectional view of a substantially planar coil apparatus for treating fluids using PDT;

FIG. 9 is a side sectional view of the substantially planar coil apparatus shown in FIG. 8;

FIG. 10 is a top perspective view, with portions in relief, showing a serpentine coil apparatus for treating fluids using PDT with a fiber optic mat light source contained therein;

FIG. 11 is a side sectional view of the apparatus shown in FIG. 10; and

DESCRIPTION OF THE PREFERRED EMBODIMENTS

As explained above, photopheresis destroys or affects an undesirable component in the blood that has absorbed a photoreactive agent having a characteristic light absorption waveband. It is believed that improved results will be obtained by administering the treatment to a patient's blood for extended periods of time in situ, using various levels of light. Moreover, relatively low intensity light sources are much less likely to cause undesired damage to other components of a patient's blood than the relatively short duration extracorporeal light therapy taught by the prior art. While all but one of the preferred embodiments of the present invention that are described below specifically mention LEDs as the preferred source of light for administering PDT to blood flow, it will be understood that other light sources are equally usable in connection with the present invention. Such alternative light sources include, but are not limited to: laser diodes, vertical cavity surface emitting lasers (VCSELs), light emitting semiconductors, gas discharge sources, light emitting polymers, and filament bulbs.

Figure 1:
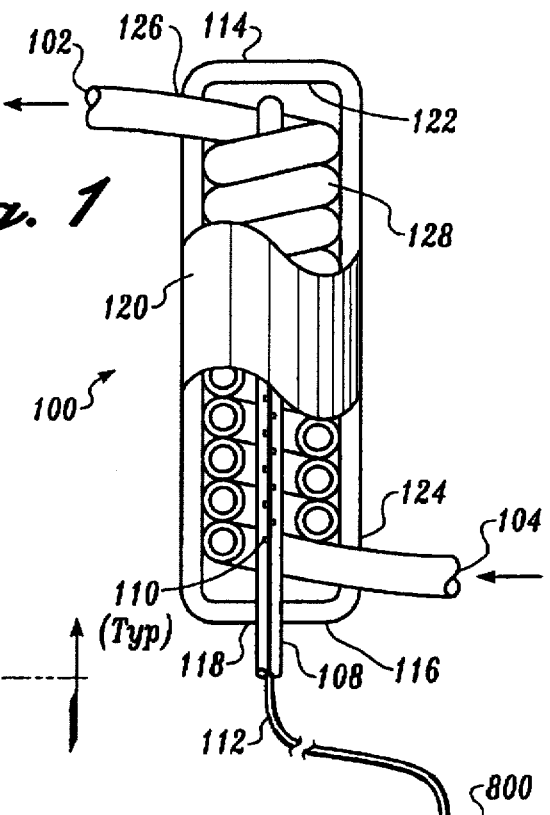
FIG. 1 is a perspective view, with portions broken away, showing a section of a helical coil apparatus for treating fluids using PDT.

Apparatus designed for administering photopheresis in situ, which are referred to generally as "reactors," are disclosed in several different embodiments, each embodiment being adapted to be transcutaneously placed at a site within a patient's body. In regard to a first embodiment of the invention, FIG. 1 shows a side sectional view of a housing 100 comprising a cylindrical wall 120 having a top end 114 and a bottom end 116 that are made of a biocompatible material, such as a TEFLON™ polymer. Alternatively, the housing can be fabricated from another material and coated with the biocompatible material. A fluid path intended for conveying blood through housing 100 comprises tubing 128 that is wound in a helical or cylindrical coiled shape. Tubing 128 is preferably a transparent (or at least translucent) material of the type that can be used for blood vessel reconstruction, such as expanded reinforced polytetrafluoroethylene (ePTFE). Also, optically transparent materials, such as polyvinyl chloride, polyurethane, and TEFLON™, can be employed for tubing 128.

Tubing 128 is disposed within housing 100 and has an inlet 104 and an outlet 102, both of which are disposed outside the housing. Specifically, inlet 104 is disposed where tubing 128 passes through an inlet aperture 124 formed within housing 100, adjacent one end, and outlet 102 is disposed where the tubing passes through an outlet aperture 126, adjacent the opposite end of the housing. Also, the diameters of inlet 104 and outlet 102 are preferably about 10 millimeters or less so that they are adaptable for grafting to the ends of a severed artery, such as the internal thoracic artery, as discussed below. Further, the diameters of inlet 104 and outlet 102 can be dissimilar to affect the velocity of the blood flow through housing 100. The curvature of tubing 128 and dissimilar diameters of inlet tube 104 and outlet tube 102 both help to induce a desirable turbulence and eddy currents in the blood flowing through housing 100. Turbulent flow of blood through the tubing within the housing also serves to increase the exposure to light that the blood passing through housing 100 receives. A light bar 108 comprising LEDs 110 (or any of the other types of light sources noted above) and a lead 112 is disposed along a center axis of tubing 128 to provide the light that irradiates the blood flowing through the housing. An end of the light bar (or at least lead 112) passes through an aperture 118, which is axially disposed in the center of end 116 of the housing.

Tubing 128 is adapted for coupling to a patient's circulatory system by the use of standard vascular anastomic techniques. A suitable artery having a diameter approximately equal to that of inlet 104 and outlet 102 is transected to permit the reactor to be placed in series with the two ends of the artery, so that the blood flowing through the artery flows through the reactor and is exposed to the light emitted by the light source contained therein. The proximal ends of inlet 104 and outlet 102 preferably have a smooth profile to facilitate fitting and grafting them to the ends of the transected artery. After coupling tubing 128 to the artery, blood is circulated from the artery into the proximal end of inlet 104, passes through housing 100 within tubing 128, out of outlet 102, and back into the artery.

LEDs 110 are energized by an electrical current conveyed through lead 112 and emit light that irradiates the blood circulating through tubing 128. Also, an interior surface 122 of housing 100 is preferably coated or lined with a reflective material such as mirrored or white MYLAR™, or any other suitable specular coating to improve the reflection of light towards the blood flowing through tubing 128.

Figure 2:
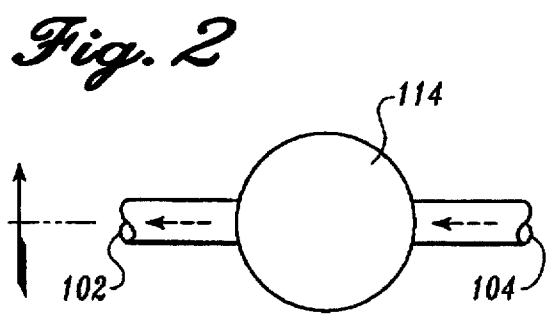
FIG. 2 is a top sectional view of the helical coil apparatus shown in FIG. 1.
Figure 3:
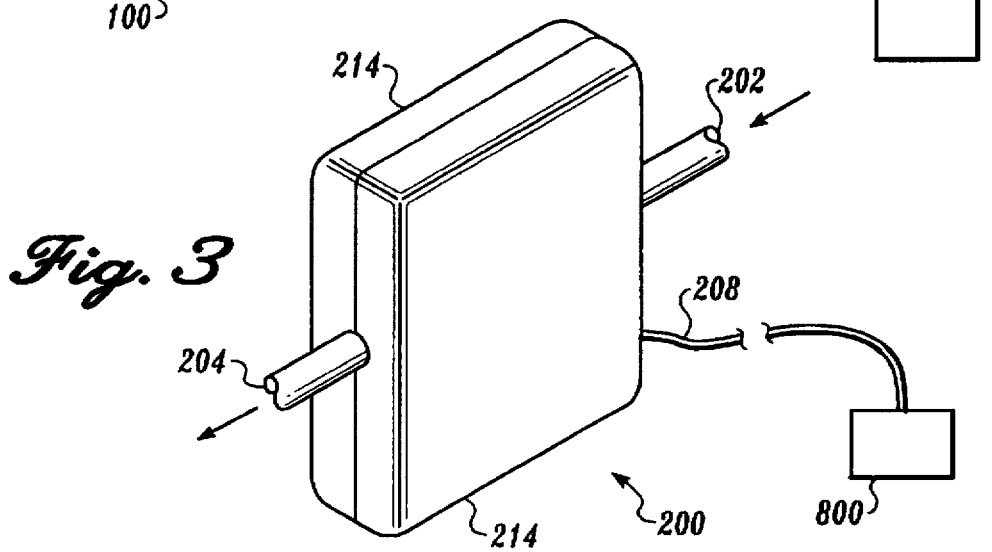
FIG. 3 is a perspective view of a reactor housing having serpentine tubing and a light source therein.

In FIG. 2, housing 100 is shown from a top view, and the compactness of its cylindrical shape is clearly evident. The compact nature of housing 100 is important when it is disposed at particular sites within a patient's body having limited space for the placement of a medical device.

Several embodiments of the present invention are illustrated in FIGS. 3 through 7. These embodiments share generally similar housings 200 and 300 having an inlet 202 and an outlet 204 projecting from the center of opposite ends of the housing in regard to the embodiment shown in FIGS. 3, 4, and 5, and an inlet 302 and an outlet 304 projecting from offset points at opposite ends of a housing 300 for the embodiment shown in FIG. 6. Housing 200 comprises a pair of sections 214 that are hermetically fastened together around inlet 202 and outlet 204 and around a lead 208. Similarly, although not separately shown, housing 300 also comprises sections that fit together and seal around inlet 302, outlet 304, and a lead 324.

Figure 7:
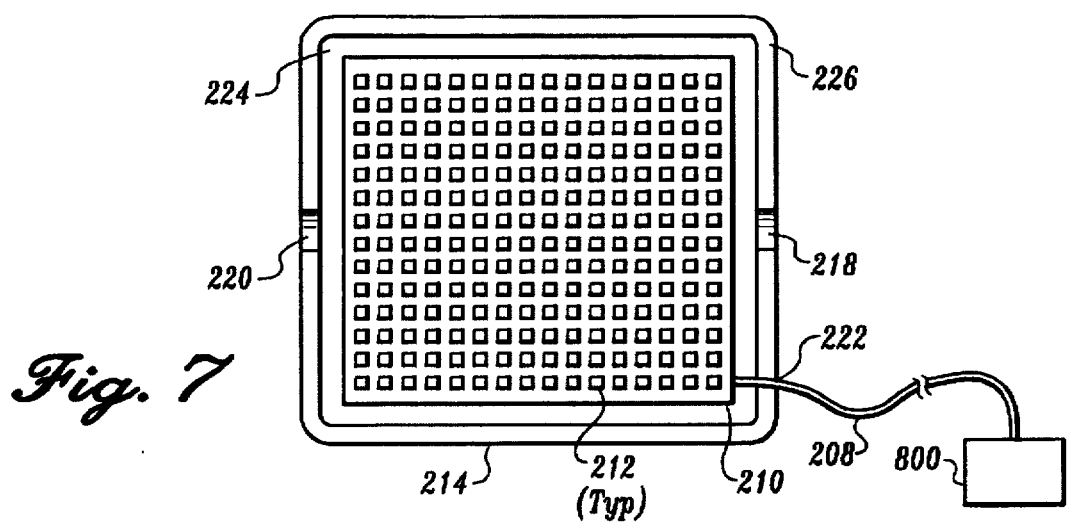
FIG. 7 is a side sectional view of a reactor housing showing an LED grid array light source installed therein.

As shown in FIG. 7, one of the two sections 214 has an outer ridge 226 that circumscribes the periphery of an interior generally planar surface 224, which is coated or lined with a reflective material such as mirrored or white Mylar. An inlet groove 218 and an outlet groove 220 accommodate, respectively, inlet 202 and outlet 204. Further, a concave groove 222 in outer ridge 226 accommodates lead 208. Also shown in this Figure is an array of spaced-apart LEDs 212 mounted on a rectangular substrate or plate 210. In this embodiment, the LEDs are the light source inside housing 200. Plate 210 is slightly smaller in size than section 214 and fits within the inside perimeter of outer ridge 226 when it is disposed adjacent to interior surface 224.

Figure 5:
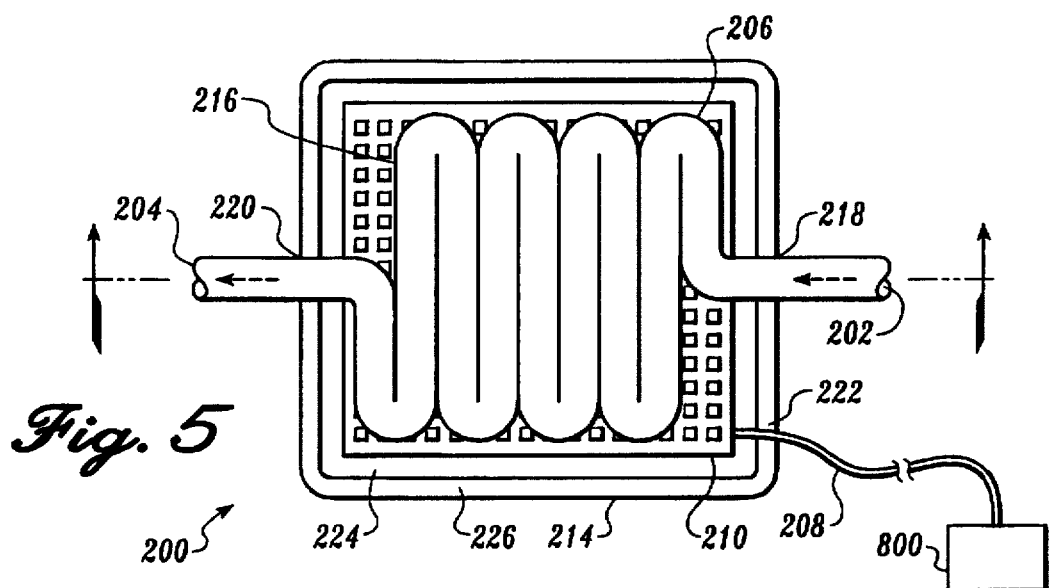
FIG. 5 is a side sectional view showing the reactor housing with tubing and light source installed therein.

Referring now to the embodiment shown in FIG. 5, a fluid path is provided through a tubing 216, that is wound in a serpentine manner comprising a series of closely spaced half circular bends 206 that are disposed on top of plate 210, against LEDs 212. Tubing 216 preferably comprises any of the materials identified above for tubing 128.

Figure 4:
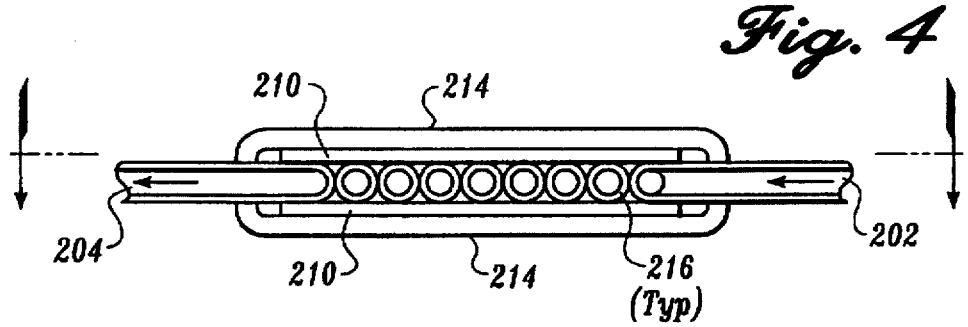
FIG. 4 is a top sectional view of the apparatus shown in FIG. 3.

In FIG. 4, a cross-sectional view of housing 200 is illustrated. Tubing 216 is shown disposed between a pair of plates 210 that are further disposed between a pair of substantially rectangular sections 214 which are held in close association to form housing 200.

As discussed above, housing 200 is similarly adaptable for coupling to a patient's circulatory system by the use of standard vascular anastomic techniques. After housing 200 has been grafted into the patient's circulatory system, the blood enters the proximal end of inlet 202 and passes through serpentine tubing 216, where it is exposed to light irradiation by LED plates 210. Once irradiated, the blood exits tubing 216 through outlet 204 and re-enters the circulatory system of the patient.

Figure 6:
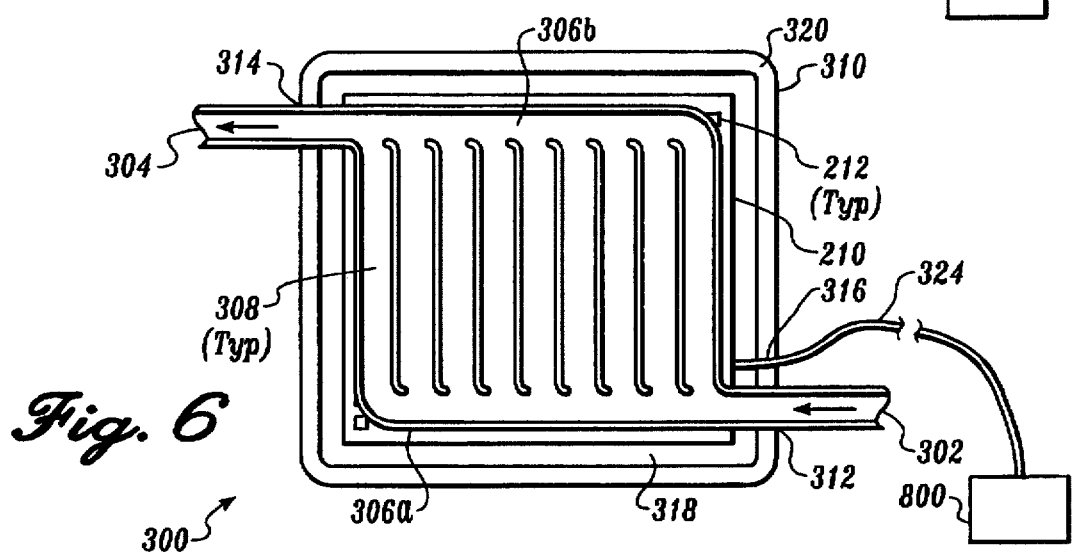
FIG. 6 is a side sectional view of the reactor housing showing a molded shape with a plurality of parallel passages extending between an inlet header and an outlet header.

An alternative embodiment providing a different fluid path for blood through housing 300 is illustrated in FIG. 6. A molded header manifold 306a is coupled to inlet 302, and a similar molded header manifold 306b is coupled to outlet 304. A plurality of parallel cross tubes 308 extend between header manifolds 306a and 306b. The header manifolds and cross tubes are made of a transparent or translucent material of the type that is commonly used for blood vessel reconstruction, such as ePTFE. Also, optically transparent materials such as polyvinyl chloride, polyurethane, and TEFLON™ can be employed to construct header manifolds 306a and 306b, and cross tubes 308.

Housing 300 is constructed in a substantially similar manner as housing 200. Housing 300 is formed from a pair of mating rectangular sections 310, each section having a concave shaped inlet groove 312, a concave shaped outlet groove 314, a lead slot 316, and an interior surface 318 that is coated or lined with a reflective material, such as mirrored or white MYLAR™. Further, light for irradiating blood flowing through housing 300 within cross tubes 308 is provided by LEDs 212 that are energized by an electrical current conveyed through lead 324. Thus, LEDs 212 are the light source inside housing 300. Sections 310 preferably comprise a biocompatible material such as a TEFLON™ polymer or are coated with such a material.

As discussed above in connection with the first embodiment, inlet 302 and outlet 304 are adapted for coupling to a patient's circulatory system by the use of standard vascular anastomic techniques. The patient's blood enters the proximal end of inlet 302 and passes through header manifold 306a into a plurality of parallel cross tubes 308, where the blood is exposed to light produced by LEDs 212. After the light-irradiated blood has passed through cross tubes 308, the blood enters header manifold 306b and leaves housing 300 through outlet 304 to re-enter the circulatory system of the patient.

Yet another alternative embodiment is illustrated in FIGS. 8 and 9. This embodiment includes a housing 400, which is generally disk shaped and comprises a top section 414 that is affixed to a similarly shaped bottom section 412. Between top section 414 and bottom section 412 is disposed a coil of tubing 406, which is wound in a substantially planar spiral. Tubing 406 is made of the same materials identified for tubing in the embodiments discussed above. Extending downwardly through bottom section 412 from an inner end of the spiraled tubing is an inlet 402; an outlet 404 extends radially outwardly through housing 400 from the outer end of the spiral. Generally round plates 408 and 424 are respectively mounted inside bottom section 412 and top section 414, so that an array of spaced-apart LEDs (not separately shown), which are mounted thereon, are disposed adjacent opposite sides of tubing 406. The LEDs are energized with an electrical current conveyed through a lead 410 from a suitable internal (or external power source (not shown). Plate 408 is slightly smaller in size than bottom section 412 and fits within the inside perimeter of a bottom outside lip 420, against an interior surface 418. Similarly, plate 424 is slightly smaller in size than top section 414 and fits within the inside perimeter of a top outside lip 426. A top outer surface 435 and a bottom outer surface 436 of housing 400 are preferably composed of a biocompatible material such as a TEFLON™ polymer. Also, a top interior surface 428 and bottom interior surface 418 are coated or lined with a reflective material such as mirrored or white MYLAR™ to improve the reflection of light towards the blood flowing through tubing 406.

Tubing 406 passes through a round inlet aperture 430, which is disposed in the center of bottom section 412. Further, tubing 406, by passing through an aperture comprising a concave groove 434 formed in top section 414, and a concave groove 432 that is formed in bottom section 412. Also, lead 410 enters housing 400 through an aperture comprising a slot 422 and a slot 416, which are respectively formed in the top and bottom sections.

As discussed above in connection with the other embodiments, inlet 402 and outlet 404 are adapted for coupling to a patient's circulatory system by the use of standard vascular anastomic techniques. The patient's blood enters the proximal end of tubing 406 through inlet 402 and passes through tubing 406 within housing 400, where the blood is exposed to light emitted by the light sources mounted on plates 408 and 424. After the light irradiated blood has passed through tubing 406, the blood exits housing 400 through outlet 404 and re-enters the circulatory system of the patient.

Yet another embodiment of the present invention is illustrated in FIGS. 10 and 11. In this embodiment, a housing 600 is coupled to an external light source 504 through a bundle 500 of optical fibers 506. Bundle 500 is divided into planar arrays 604 and 608, each of which includes optical fibers 506 that enter housing 600 along one side of either a top section 606 or a bottom section 602, at spaced-apart points. Ends of optical fibers 506 comprising planar array 604 are terminated along one edge of a top mat 508. Similarly, ends of optical fibers 506 comprising planar array 608 are terminated along one edge of a bottom mat 510. Thus, light conveyed through the optical fibers passes through the ends of the optical fibers and is diffused through the top and bottom mats. The light conveyed through the top and bottom mats irradiates blood flowing through a path within housing 600. Tubing 216, having a serpentine shape, is shown within housing 600 in the Figures; however, the optical fibers can be used to convey light that irradiates blood flowing through any of the other configurations for a fluid path through any of the reactors that are discussed above.

In FIG. 11, the tubing conveying blood is disposed between top mat 508 and bottom mat 510, respectively within top section 606 and bottom section 602. Since top mat 508 and bottom mat 510 convey light received from optical fibers 506, which is produced by external light source 504, the top and bottom mats have a much lower operating temperature than a light source that is included inside any of the housings discussed above. Additionally, a top interior surface 612 and a bottom interior surface 610 are coated or lined with a reflective material such as white or mirrored MYLAR™ to enhance the delivery of light to the blood flowing through the reactor. Also, a top outside surface 616 and a bottom outside surface 614 are typically fabricated of or coated with a biocompatible material such as TEFLON™.

Figure 12:
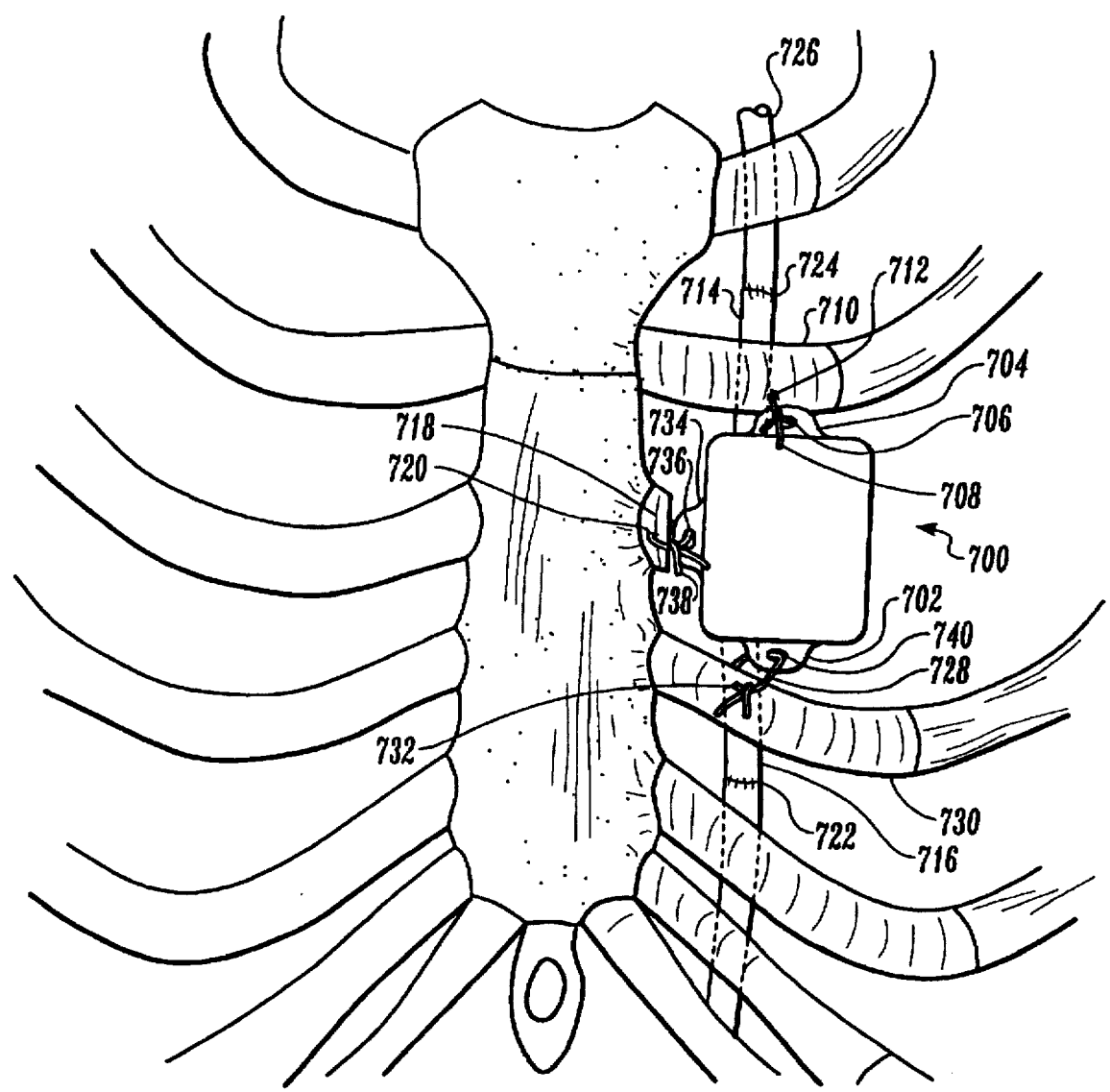
FIG. 12 is a perspective view showing a biocompatible reactor housing containing an apparatus for treating fluids using PDT, and showing the apparatus disposed inside a patient's rib cage.

While any of the embodiments of the present invention discussed above can be implanted at other sites within a patient's body, a particularly suitable site is within the thoracic cavity, adjacent to the sternum. This site provides access to the internal thoracic artery, which can readily be transected to enable the reactor to be attached in series with the transected ends of the artery, without significant adverse effects on the patient. In the implantation process, which is illustrated in FIG. 12, the left third true rib is removed and costal cartilage 718 is trimmed to accommodate the positioning of a housing 700 within the resulting cavity. Housing 700 is intended to be merely representative of the housings of any of the embodiments discussed above. An inlet 714 and an outlet 716, which are also representative of the inlet and outlet for any of the embodiments discussed above, extend from the housing and are attached to the ends of severed internal thoracic artery 726 at a top suture line 724 and a bottom suture line 722, so that blood flowing through the internal thoracic artery is shunted through housing 700. Once housing 700 is tied into the patient's circulatory system and securely positioned as described below, PDT can be administered to the blood flowing through the reactor on either a continuous or intermittent basis, simply by energizing the light source(s).

The housings of any of the embodiments discussed above may include one or more tabs for securing the housing to a desired location within the patient's body. In FIG. 12, housing 700 has tabs disposed on three of its four edges. A top tab 704 is disposed on the top edge of housing 700 and has an aperture 706 through which a suture 708 is threaded. A costal cartilage 710 for the left second true rib is perforated to form a suture aperture 712 through which suture 708 is looped and tied to secure housing 700. This attachment procedure is optionally repeated for a bottom tab 702 that is disposed on the bottom edge of housing 700. Bottom tab 702 has an aperture 740 through which a suture 728 is threaded. Subsequently, a costal cartilage 730 for the left fourth true rib is perforated to form a suture aperture 732 through which suture 728 is looped and tied to securely position housing 700. The attachment of a side tab 734 to a patient's body is accomplished in a similar manner. Side tab 734 has an aperture 736 through which a suture 738 is threaded. Trimmed costal cartilage 718 is perforated to form a suture aperture 720 through which suture 738 is looped and tied to securely position housing 700 within the patient's body.

All of the leads in the various embodiments are connected to a matched power supply 800 capable of supplying an electrical current to energize the various types of light sources discussed above. Power supply 800 is preferably an intracorporeal device that is disposed in situ near the reactor, however, it may also be located external to the patient's body. Further, the power supply can be disposed within the housing to provide the electrical current necessary to energize the light sources. In any case, the power supply can comprise a rechargeable battery and/or be inductively coupled to an external source that electromagnetically supplies power to the internal power supply.

Although not shown in any of the embodiments described herein, electroluminescent panels can be used as the source of light that irradiates blood flowing through any of the reactor housings. These panels would be disposed on opposite sides of the path along which blood flows through the housing.

The light sources described in the various embodiments above irradiate the patient's blood from a location inside the reactor housing. However, the light sources can be coupled to the exterior surface of the reactor so that the blood flowing through a fluid within the housing irradiated with light from the sources that passes through a transparent (or at least translucent) housing. An externally positioned light source could also have a backing that is coated or lined with a reflective material such as white or mirrored MYLAR™ to enhance the delivery of light to the blood flowing through the reactor.

Another aspect of the present invention is directed to reducing skin photosensitivity that can occur as a result of intravenous drug delivery of the photosensitizer. The photosensitizer may be administered intra-arterially using a drug pump that injects the photosensitizer into the patient's circulatory system at a point that is just proximal to the site of the reactor. With this approach, the drug should be mostly photobleached by the light administered in the housing before the drug exits the reactor. A reservoir of the photosensitizer drug could also be coupled by a tube to the inlet of the reactor and allowed to elute into the blood flow via a porous tip.

An inherent advantage of the present invention is that excessive heat buildup from the light source is prevented by the continual flow of blood through the housing. The total length of the fluid path through the housing extends the circulation time of the patient's blood within the reactor and thus prolongs the duration of the PDT. Further, the proper selection and targeting of photosensitizer drugs may cause selective binding to occur to the pathogen and avoid photodynamic injury to normal blood constituents.

An added benefit is that the photodynamic action on the inner wall of the fluid path through the reactor housing may prevent intimal hyperplasia, which could lead to failure of the graft of a blood vessel to the inlet or outlet of the reactor. Also, the inner walls of the fluid path through which blood flows through the reactor may be lined with an anticoagulant, such as heparin, so as to prevent the clotting of blood cells in the housing. However, it is possible that simply administering a low dose of aspirin after the reactor is implanted may provide sufficient thinning of the blood to prevent clotting within the fluid path of the reactor.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for administering intracorporeal photopheresis to blood flowing in a patient's body to destroy or affect an undesirable component in the blood, where the undesirable component has absorbed a photoreactive agent having a characteristic light absorption waveband, said apparatus comprising:
   (a) an implantable housing adapted to be transcutaneously placed at a site within a patient's body, said implantable housing comprising a biocompatible material and having an inlet port and an outlet port adapted to couple to a patient's circulatory system to convey the blood circulated thereby into and out of the housing;
   (b) a light source coupled to the housing, said light source emitting light within a waveband substantially equal to the absorption waveband of the photoreactive agent;
   (c) a power source for supplying an electrical current to energize said light source; and
   (d) a fluid path disposed within the housing adjacent to the light source and in fluid communication with said inlet port and said outlet port, at least a portion of said fluid path being optically transparent, so that blood circulating through the fluid path is irradiated with the light emitted by said light source to effect the light treatment, said blood circulating through the fluid path sufficiently fast to avoid heat build up that might otherwise harm the blood.

2. The apparatus of claim 1, wherein the fluid path comprises a serpentine shaped passage.

3. The apparatus of claim 1, wherein the fluid path comprises a helically coiled passage.

4. The apparatus of claim 1, wherein the fluid path is a substantially planar coil.

5. The apparatus of claim 1, wherein the fluid path comprises a plurality of parallel passages extending between two headers, one of said two headers being coupled to the inlet port and another of the two headers being coupled to the outlet port.

6. The apparatus of claim 1, wherein the light source comprises one of a first generally planar array of spaced-apart light emitting devices and a luminescent panel.

7. The apparatus of claim 6, wherein the light source further comprises a second generally planar array of spaced-apart light emitting devices, said first and said second arrays being disposed at opposite sides of the fluid path with the light emitting devices being directed to emit light toward the fluid path.

8. The apparatus of claim 6, wherein the light emitting devices are mounted on a substantially light reflecting surface.

9. The apparatus of claim 1, wherein the light source comprises a bar that includes a plurality of light emitting devices that are spaced apart generally along a longitudinal axis of the bar.

10. The apparatus of claim 1, wherein the light source comprises a plurality of optical fibers coupled to a light emitting device.

11. The apparatus of claim 1, wherein the power source is integral with the housing.

12. The apparatus of claim 1, wherein the power source is disposed within an enclosure comprising a biocompatible material and is thus adapted to be implanted within the patient's body, separate from the housing.

13. The apparatus of claim 1, wherein the housing includes a tab usable for securing the housing at a desired location within the patient's body.

14. The apparatus of claim 1, wherein the housing has a substantially light reflective inner surface.

15. The apparatus of claim 1, wherein the inlet port and the outlet port comprise vascular graft tubing.

16. The apparatus of claim 1, wherein an inner surface of the fluid path is coated with a medicinal substance that resists formation of blood clots.

17. A method for treating blood flowing in a patient's body to destroy an undesirable component in the patient's blood, comprising the steps of:
   (a) administering a photoreactive agent to the patient, said photoreactive agent being absorbed by the undesirable component in the blood and having a characteristic light absorption waveband;
   (b) providing an implantable photoreactor having a light source for use in exposing the blood within the patient's body to light having a waveband substantially equal to the characteristic light absorption waveband of the photoreactive agent;
   (c) creating a surgical incision within the patient's body to expose a site for implantation of the photoreactor;
   (d) coupling the implantable reactor into the patient's circulatory system so that the patient's blood circulates through the implantable reactor;
   (e) closing the surgical incision over the implantable reactor, leaving it at the site internally within the patient's body; and (f) exposing the blood circulating through the photoreactor to the light from the light source within the photoreactor in order to destroy or adversely affect the undesirable component, said blood circulating through the fluid path sufficiently fast to avoid heat build up that might otherwise harm the blood.

18. The method of claim 17, wherein the step of creating a surgical incision further includes the step of removing a section of a rib to gain access to the patient's circulatory system and to provide the site for the photoreactor.

19. The method of claim 17, wherein the step of coupling the implantable reactor into the patient's circulatory system includes the step of transecting a blood vessel to couple ends of the blood vessel to the photoreactor, so that the blood flowing through the blood vessel flows through the photoreactor.

20. The method of claim 17, wherein the step of exposing comprises the step of circulating the blood through the photoreactor through one of serpentine tubing, planar coiled tubing, tubing extending between two headers, and helically coiled tubing, thereby providing a greater exposure of the blood to the light as the blood flows through the photoreactor.

21. The method of claim 17, wherein the housing includes vascular graft tubing at an inlet port and an outlet port, said step of coupling comprising the step of suturing the vascular graft tubing into a blood vessel within the patient's body, said vascular graft tubing conveying the blood flowing through the blood vessel into and out from the photoreactor via the inlet port and the outlet port, respectively.

22. The method of claim 17, further comprising the step of attaching the photoreactor to tissue in the patient's body to secure the photoreactor at said site.

23. The method of claim 17, wherein the blood circulating through the photoreactor is exposed to light from a plurality of light emitting devices that are coupled to the photoreactor.

24. The method of claim 17, wherein the blood circulating through the reactor is exposed to light from opposite sides.

25. The method of claim 17, further comprising the step of infusing an anti-clotting medicinal substance into the blood as the blood circulates through the photoreactor.

26. The method of claim 17, further comprising the step of coupling power to a power supply implanted within the patient's body from an external source, said power supply being used to electrically energize the photoreactor.

* * * * *